(12) United States Patent
Posthuma

(10) Patent No.: US 6,231,574 B1
(45) Date of Patent: May 15, 2001

(54) BIPOLAR FORCEPS

(75) Inventor: Adriaan Osmond Posthuma, Sheffield (GB)

(73) Assignee: Uniplex Limited (GB)

( * ) Notice: Subject to any disclaimer, the term of this patent is extended or adjusted under 35 U.S.C. 154(b) by 0 days.

(21) Appl. No.: 09/426,630

(22) Filed: Oct. 26, 1999

(30) Foreign Application Priority Data

Oct. 28, 1998 (GB) ................................... 9823490

(51) Int. Cl.$^7$ ................................... A61B 18/12
(52) U.S. Cl. ................................... 606/51
(58) Field of Search ................................... 606/51, 52, 48, 606/50; 439/709, 722

(56) References Cited

U.S. PATENT DOCUMENTS

| | | |
|---|---|---|
| 4,732,149 | 3/1988 | Sutter . |
| 4,890,610 * | 1/1990 | Kirwan et al. ................ 606/51 |
| 5,196,009 | 3/1993 | Kirwan, Jr. . |

* cited by examiner

Primary Examiner—Michael H. Thaler
(74) Attorney, Agent, or Firm—Trexler, Bushnell, Giangiorgi, Blackstone & Marr, Ltd.

(57) ABSTRACT

Bipolar forceps in which each of two limbs (10, 11) is formed by a length of stainless steel (12, 13) extending from an exposed pointed tip portion (14, 15) through an electrically-insulating ribbed grip portion (16, 17) to an exposed terminal portion, the terminal portions (18, 19) of the two limbs being separated by intervening electrically-insulating material (20), and the terminal portions and intervening electrically-insulating material form a plug (21) for insertion into a 'Block' fitting attached to a cable for connecting to a power supply, and wherein each length of stainless steel (12, 13) is formed of wire and a unitary moulding of electrically-insulating material forms both grip portions (16, 17) and shoulder portions (39, 40) for the plug (21), with the lengths of stainless steel wire (12, 13) enclosed in the grip portions (16, 17) and in the shoulder portions (39, 40), in which shoulder portions the wires are bent to bring their terminal portions (18, 19) into close parallel disposition in the plug.

8 Claims, 1 Drawing Sheet

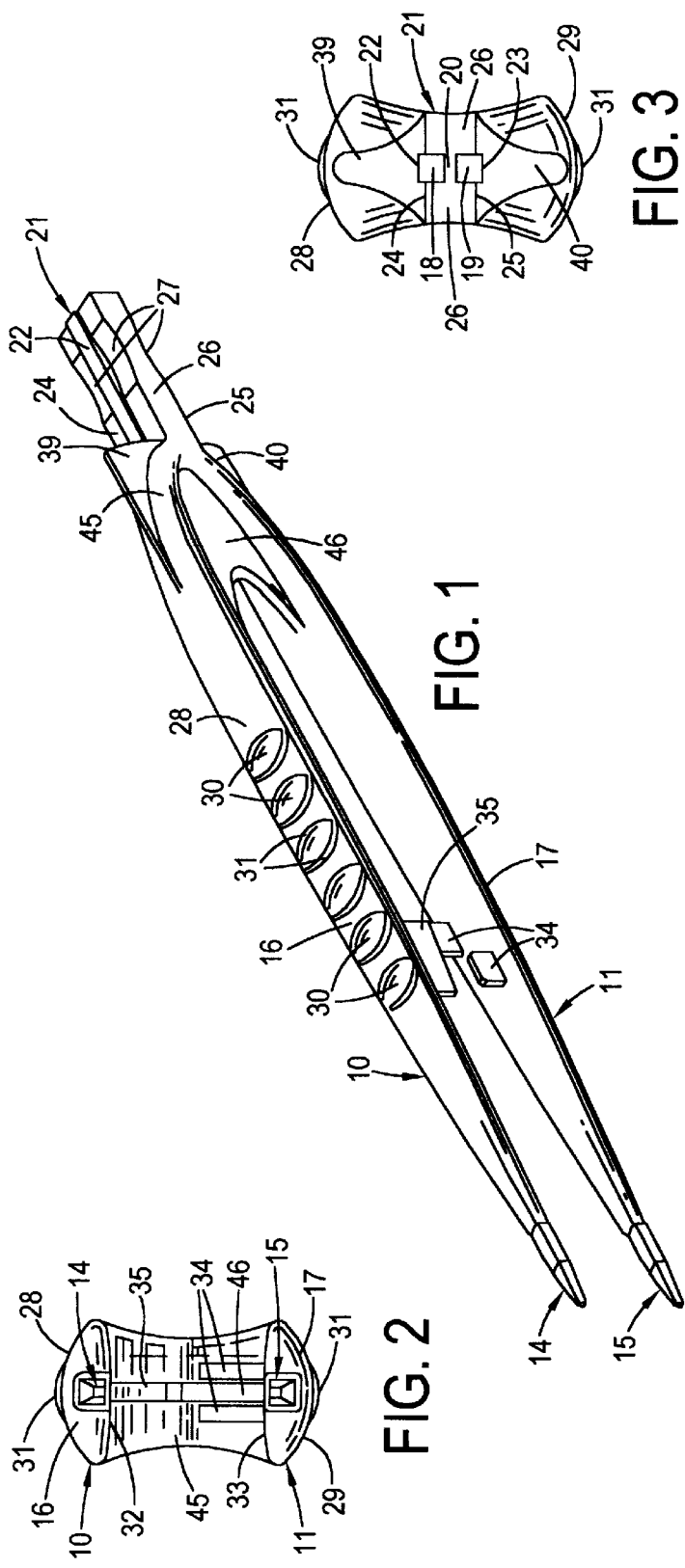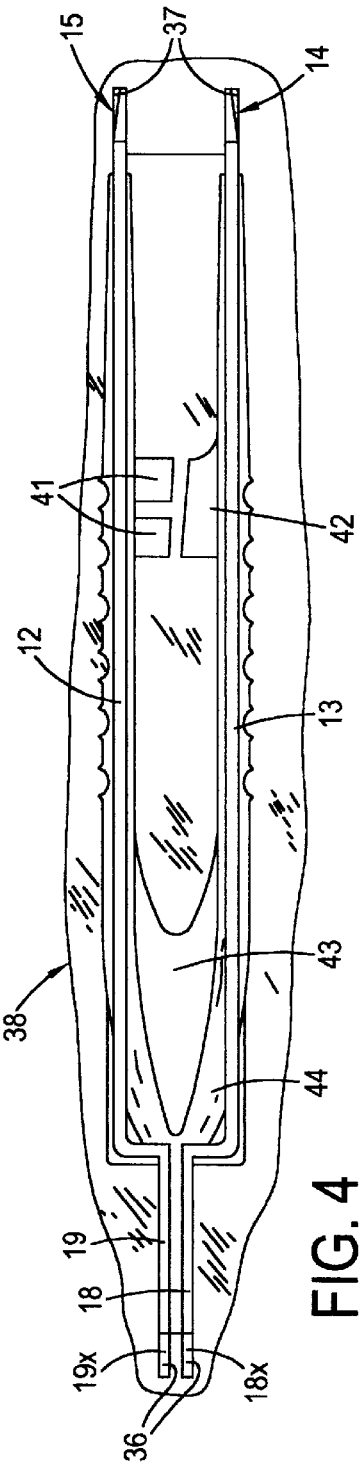

BIPOLAR FORCEPS

This invention relates to bipolar forceps such as are used in electrosurgery and in which each of two limbs is formed by a length of stainless steel extending from an exposed pointed tip portion through an electrically-insulating ribbed grip portion to an exposed terminal portion, the terminal portions of the two limbs being separated by intervening electrically-insulating material, and the terminal portions and intervening electrically-insulating material form a plug for insertion into a 'Block' fitting attached to a cable for connecting to a power supply.

In bipolar forceps known as the 'Downs Eschmann Forceps' stainless steel strip is used to form the basis of each limb, having a major length with parallel edges forming the terminal portion and the basis of the grip portion, and a minor length tapering from the grip portion to the exposed tip, with electrically insulating material enclosing the stainless steel strip from closely adjacent the tip along the grip portion and terminating in a cylindrical collar providing an annular shoulder on the plug for abutment against the 'Block' fitting into which the plug will be inserted.

Manufacture of the 'Downs Eschmann Forceps' involves an appreciable number of operations, including punching out the stainless steel strips with tapering lengths at one end and holes in the terminal portions at the other end for securing (in another operation) to the intervening electrically-insulating material, coating the shaped strips with electrically-insulating material, moulding the ribbed grip portions, and moulding the collar on the plug, all of which incurs considerable expense not conducive to these forceps being disposable.

The object of the present invention, is therefore, to provide a construction and method of manufacture of bipolar forceps the cost of which is conducive to the forceps being disposable.

According to the present invention, bipolar forceps of the type initially described are characterized in that each length of stainless steel is formed of wire (preferably of rectangular cross-section, and more particularly square), and a unitary moulding of electrically-insulating material forms both grip portions and shoulder portions for the plug, with the lengths of stainless steel wire enclosed in the grip portions and in the shoulder portions, in which shoulder portions the wires are bent to bring their terminal portions into close parallel disposition in the plug.

The terminal portions of the wires are preferably initially of a length slightly in excess of the length of the plug, so that during manufacture those excess lengths and the pointed tip portions can be located in recesses in the ends of mould parts into which the electrically-insulating material is injected, and the excess lengths are cropped off after removing the co-moulded forceps from the mould. A suitable insulating material is Nylon 66. The insulating material in the plug preferably has an H cross-section with the terminal portions of the wires separated by the crossbar of the H and the oppositely-facing sides of the terminal portions flush with or slightly raised from the respective upper and lower faces of the uprights of the H. The insulating material preferably has shallow indentations in the upper and lower faces of the uprights of the H, for snap engagement in a 'Block' fitting attached to a cable for connecting to a power supply The oppositely-facing sides of the grip portions are preferably provided with series of moulded cross-grooves with slightly raised edges to afford a good grip; and the mutually-facing sides of the grip portions are preferably provided with two laterally spaced projections on one side and one intervening projection on the other side, to ensure correct alignment of the pointed tips when the forceps are squeezed together.

An embodiment of the invention will now be described, by way of example only, with reference to the accompanying drawings, in which:

FIG. 1 is a perspective view of bipolar forceps in accordance with the invention;

FIG. 2 is an enlarged elevation taken from the left hand end of FIG. 1;

FIG. 3 is an enlarged elevation taken from the right hand end of FIG. 1; and

FIG. 4 is a fragmentary view of a mould part showing in place stainless steel wires only the ends of which are visible in FIGS. 1 to 3.

The bipolar forceps shown in FIGS. 1 to 3 comprise two limbs 10, 11 formed by lengths, 12, 13 of square-section stainless steel wire (see also FIG. 4) extending from exposed pointed tips 14, 15 through electrically-insulating grip portions 16, 17 to exposed terminal portions 18, 19 separated by an intervening portion 20 of the electrically insulating material of a plug 21, and the portion 20 is the crossbar of an H-section, with the oppositely-facing sides 22, 23 of the terminal portions 18, 19 of the wires slightly raised from the respective upper and lower faces 24, 25 of the uprights 26 of the H. These upper and lower faces of the uprights of the H have shallow indentations 27 for snap engagement in a 'Block' fitting (not shown) attached to a cable for connecting to a power supply.

The oppositely-facing sides 28, 29 of the grip portions 16, 17 are provided with series of moulded cross-grooves 30 with slightly raised edges 31 to afford a good grip; and the mutually-facing sides 32, 33 of the grip portions are provided with two laterally spaced projections 34 on one side and one intervening projection 35 on the other side to ensure correct alignment of the pointed tips 14, 15 when the forceps are squeezed together.

The terminal portions 18, 19 of the wires 12, 13 are initially of a length slightly in excess of the length of the plug 21, so that during manufacture those excess lengths 18X, 19X and the pointed tip portions 14, 15 can be located in recesses 36, 37 in the respective ends of mould parts 38 (only one of which is shown in FIG. 4) into which the electrically-insulating material is injected, and the excess lengths are cropped off after removing the co-moulded forceps from the mould.

A suitable insulating material is Nylon 66 and the mould part 38 in FIG. 4 shows cavity formations for forming the unitary moulding complete with the grip portions 16, 17 and shoulder portions 39, 40 for the plug 21 in which shoulder portions the wires 12, 13 are each bent through opposite angles of 90° to bring their terminal portions 18, 19 into close parallel disposition in the plug. FIG. 4 also shows formations 41, 42 for forming the projections 34, 35 and formations 43, 44 for forming respectively a bow 45 between the grip portions 16, 17 and the plug 21 and a web 46 between the grip portions.

What is claimed is:

1. Bipolar forceps in which each of two limbs is formed by a length of stainless steel extending from an exposed pointed tip portion through an electrically-insulating ribbed grip portion to an exposed terminal portion, the terminal portions of the two limbs being separated by intervening electrically-insulating material, and the terminal portions and intervening electrically-insulating material form a plug for insertion into a socket attached to a cable for connecting to a power supply, wherein each length of stainless steel is formed of wire of rectangular cross-section and a unitary moulding of electrically-insulating material forms both grip portions and shoulder portions for the plug, with the lengths of stainless steel wire enclosed in the grip portions and in the shoulder portions, in which shoulder portions the wires are bent towards each other to bring their terminal portions into close parallel disposition in the plug, and wherein the insulating material in the plug has an H cross-section with the terminal portions of the wires separated by the crossbar of the H.

2. Bipolar forceps as in claim 1, wherein the wire is of square cross-section.

3. Bipolar forceps as in claim 1, wherein the terminal portions of the wires are initially of a length slightly in excess of the length of the plug, so that during manufacture those excess lengths and the pointed tip portions can be located in recesses in the ends of mould parts into which the electrically-insulating material is injected, and the excess lengths are cropped off after removing the co-moulded forceps from the mould.

4. Bipolar forceps as in claim 1, wherein the electrically-insulated material is Nylon 66.

5. Bipolar forceps as in claim 1, wherein the oppositely-facing sides of the terminal portions are slightly raised from the respective upper and lower faces of the uprights of the H.

6. Bipolar forceps as in claim 5, wherein the insulating material has shallow indentations in the upper and lower faces of the uprights of the H, for snap engagement in a socket attached to a cable for connecting to a power supply.

7. Bipolar forceps as in claim 1, wherein the oppositely facing sides of the grip portions are provided with series of moulded cross-grooves with slightly raised edges to afford a good grip.

8. Bipolar forceps as in claim 1, wherein the mutually-facing sides of the grip portions are provided with two laterally spaced projections on one side and one intervening projection on the other side, to ensure correct alignment of the pointed tips when the forceps are squeezed together.

* * * * *